United States Patent [19]

Karpov et al.

[11] 4,365,969
[45] Dec. 28, 1982

[54] METHOD FOR QUANTITATIVE ANALYSIS OF CHEMICAL COMPOSITION OF INORGANIC MATERIAL

[76] Inventors: Jury A. Karpov, ulitsa Svobody, 3, kv. 44, Moscow; Boris P. Burylev, ulitsa Moskovskaya, 2, korpus 1, kv. 117, Krasnodar; German G. Glavin, Profsojuznaya ulitsa, 33, kv. 155; Valeria E. Kvin, Lipetskaya ulitsa, 20, kv. 336, both of Moscow; Vasily V. Kovalev, Shemonaikhinsky raion, poselok Pervomaisky, ulitsa Metallurgov, 3, kv. 56, Vostochno-Kazakhstanskaya oblast; Konstantin J. Natanson, 3 Dorozhny proezd, 9, korpus 1, kv. 107, Moscow; Vladimir V. Orlov, I Koptelsky pereulok, 14, kv. 20, Moscow; Lev B. Kuznetsov, Rostovskaya naberezhnaya, 5, kv. 245, Moscow; Anatoly M. Zaitsev, Leninsky prospekt, 52, kv. 87, Moscow; Valentin E. Kartsev, ulitsa Ostrovityanova, 41, korpus 1, kv. 323, Moscow; Vladimir M. Morozov, Dobroslobodskaya ulitsa, 16, korpus 3, kv. 17, Moscow; Gennady G. Kovalev, Tashkentskaya ulitsa, 16, korpus 1, kv. 21, Moscow, all of U.S.S.R.

[21] Appl. No.: 222,506

[22] Filed: Jan. 5, 1981

[51] Int. Cl.$^3$ .......................................... G01N 31/00
[52] U.S. Cl. ..................................... 436/75; 422/80; 436/73
[58] Field of Search ..................... 23/230 R, 230 PC

[56] References Cited

FOREIGN PATENT DOCUMENTS 154239  7/1963  U.S.S.R. ............................ 23/230 P
416573 11/1974  U.S.S.R. ............................ 23/230 R

OTHER PUBLICATIONS

Analytical Chem. of Phosphorous; V. I. Vernadsky Inst. of Geochem. & Analyt. Chem.; Moscow, 1974.
An Analysis of Gases in Metals; Turovtseva et al.; U.S.S.R. Academy of Sciences, 1959.
The Analytical Chem. of Fluorine; Nikolaev et al.; U.S.S.R. Academy of Sciences, 1970.
The Analytical Chem. of Silicon; Myshlayeva; U.S.S.R. Acad. of Sciences.
Oxid. Vacuum Fusion–Is a New Method for the Deter. of Carbon in Metals; Karpov; Moscow, 1974.
Kinetics and Thermodynamics of Interaction of Gases with Molten Metals, Nauka Pub. Moscow, 1974.

*Primary Examiner*—Michael S. Marcus
*Attorney, Agent, or Firm*—Lilling & Greenspan

[57] ABSTRACT

A method for quantitative analysis of the chemical composition of an inorganic material comprising extraction of the element being determined from a sample of the inorganic material into the gas phase by treating the sample with a reagent that forms, with the element being determined, a volatile halide that is quantitatively analyzed in the gas phase. The method of this invention enables the determination of a broad range of elements. It is possible to determine one, two and more elements in a single experiment. The method is highly sensitive. The lower limit of detection of elements is $10^{-5}$ to $10^{-7}\%$. The accuracy of determination of elements present in concentrations of $10^{-5}$ to $10^{-6}\%$ ranges from 15 to 30%.

18 Claims, No Drawings

METHOD FOR QUANTITATIVE ANALYSIS OF CHEMICAL COMPOSITION OF INORGANIC MATERIAL

FIELD OF THE INVENTION

The present invention relates to the investigation of chemical and physical properties of substances and, more specifically, to methods for analyzing inorganic materials for the content of elements forming volatile compounds. The term "inorganic materials" as used hereinafter denotes metals, alloys, metal compounds (oxides, hydroxides, salts, carbides, nitrides, silicides, borides, phosphides and the like), metalloids, and compounds of metalloids such as boron phosphide and boron carbide.

BACKGROUND OF THE INVENTION

Numerous chemical, spectral and X-ray methods are currently used in analytical chemistry for the quantitative analysis of inorganic materials. Method for determining individual elements can be found in periodicals issued by "Nauka" Publishing House in the series "Analytical Chemistry of Elements," for example, "Analytical Chemistry of Fluorine," Moscow, 1970; "Analytical Chemistry of Silicon," 1972; and "Analytical Chemistry of Phosphorus," Moscow, 1974.

Chemical methods of analysis have disadvantages, for example, in their specificity, i.e., their applicability in every particular case to the determination of one element only, and the laborious nature of the test procedures. Disadvantages of spectral methods include poor accuracy and insufficient sensitivity relative to certain elements. X-ray diffraction analysis methods have poor sensitivity and necessitate the use of sophisticated and expensive equipment.

Known in the art is a method for quantitative analysis of a chemical composition of an inorganic material or a method of high-temperature vacuum extraction for the determination of oxygen and carbon comprising dissolution of a sample of the inorganic material in a bath of a metal salt saturated with a reagent, which is carbon in the case of oxygen determination, and which is oxygen in the case of determination. Oxygen or carbon is extracted from the melt to the gas phase in the form of gaseous carbon monoxide formed in the melt via the reaction of oxygen of the material sample and the bath carbon (in the determination of oxygen) or carbon of the material sample and the bath oxygen (in the determination of carbon), followed by the quantitative determination of carbon monoxide in the gas phase (cf. Z. M. Turovtzeva, L. L. Kunin "Analysis of Gases in Metals," Moscow, USSR Academy of Sciences Publishing House, 1959; Y. A. Carpov, K. Y. Natanson, coll. "Kinetics and Thermodynamics of Interaction of Gases with Liquid Metals," Moscow, "Nauka" Publishing House, 1974, pp. 182-185).

The above method makes it possible to carry-out the quantitative analysis of a broad range of inorganic materials. The sensitivity of the determination of oxygen or carbon is $10^{-4}$ to $10^{-5}\%$. The accuracy of the determination of said elements in concentrations within the range of from $10^{-4}$ to $10^{-5}\%$ equal to 15-20%. A disadvantage of the high-temperature vacuum extraction method resides in its specificity, i.e., it can only be used for the determination of a single element in every particular case, as well as a limited range of the elements being determined. At present, this prior art method can be used only in the analytical chemistry of gaseous elements and carbon.

SUMMARY OF THE INVENTION

It is an object of the present invention to provide a method for quantitative analysis of a chemical composition of inorganic materials based on a high-temperature extraction of the element being determined, into the gas phase which enables the determination of a broad range of elements at a high sensitivity and accuracy.

This and other objects of the present invention are accomplished by a method for the quantitative analysis of a chemical composition of an inorganic material comprising extracting of the element being determined into the gas phase from a sample of the inorganic material, followed by its quantitative determination in the gas phase, wherein, according to the present invention, the extraction of the determined element from the sample of the inorganic material is effected by treating said sample with a reagent which forms with the determined element a volatile halide evolving into the gas phase.

Using the method according to the present invention, it is possible to recover to the gas phase and quantitatively determine the elements forming volatile halides such as fluorides or chlorides, namely: Al, As, B, C, Cr, Ge, Ga, Ir, Mo, Nb, Os, P, Pd, Re, Ru, Pb, Sb, Si, Sn, Ta, Ti, Te, U, V, W, Hg, Mn, as well as fluorine and chlorine. When selective gas-analyzers are used such as a mass-spectrometer in one sample of an inorganic material in a single experiment there can be performed a determination of one, two and more elements forming volatile halides. Therefore, it becomes possible to carry out a multi-element analysis. The method according to the present invention features high sensitivity: the lower limit of detection of elements is $10^{-5}$ to $10^{-7}\%$ which for the majority of elements is by 1-2 orders of magnitude higher than the sensitivity of the methods currently employed for the determination of the above-mentioned elements. The accuracy of determination of these elements at concentrations within the range of from $10^{-5}$ to $10^{-6}\%$ is 15 to 30%. The method according to the present invention is rather rapid: the total duration of the treatment of a sample with a reagent forming a volatile halide with the element being determined, extracting the volatile halide into the gas phase and quantitative determination of the element in the gas phase is 5 to 10 minutes.

The reagents forming a volatile halide with the element being determined in the determination of Al, As, B, C, Cr, Ge, Ga, Ir, Mo, Nb, Os, P, Pd, Re, Ru, Pb, Sb, Si, Sn, Ta, Te, Ti, U, V, W, Hg, Mn can be non-volatile halides such as fluorides of rare-earth, alkali-earth and transition metals; chlorides of rare-earth, alkali-earth or alkali metals, as well as complex fluorides of alkali metals such as fluoroniobate, fluorotitanate or fluorotantalate of an alkali metal, or mixtures of said salts. The treatment of a sample of an inorganic material in the determination of the above-mentioned elements is conducted, according to the present invention, either by dissolution of a sample in a bath of a metal melt with the formation of a layer of a melt of a reagent—a nonvolatile metal halide on the surface of the bath, or by dissolution of the sample in a melt of a reagent—complex fluorides of alkali metals, or by intermixing a preliminarily disintegrated sample with a powder of a reagent—nonvolatile metal halide such as nickel fluoride, cobalt fluoride or sodium chloride, followed by heat-treatment of the resulting mixture at a temperature ranging from 500° to 800° C. under vacuum of $1 \times 10^{-6}$ to $5 \times 10^{-6}$ mm Hg.

In the case where the treatment of a sample of an inorganic material is effected by dissolution of the sample in a bath of a metal melt with the formation of a layer of the reagent melt on its surface, it is advisable, for increasing the sensitivity and accuracy of the analysis, to prepare the metal melt bath by fusing the metal in a crucible made of a fluorine-containing material such as fluorphlogopite of the composition $KMg_3AlSi_3O_{10}F_2$. The crucible is preliminarily heat-treatment at a temperature 100°–150° C. lower than the melting point of the crucible material and under vacuum of from $10^{-3}$ to $10^{-4}$ mm Hg.

In the case where the reagent used is made of complex fluorides of alkali metals, with the intention of lowering the temperature and stabilizing the conditions of the extraction process, it is advisable to treat the sample of the inorganic material by way of dissolution of the sample in a melt of the complex fluorides of alkali metals containing a chloride of at least one alkali metal in an amount ranging from 4 to 90% of the total weight of the melt.

In the determination of fluorine and/or chlorine, the reagent forming a volatile halide with the element being determined can be made of silicon-containing metal melts and the treatment of the sample of inorganic material is conducted by dissolving the sample in the silicon-containing melt.

It is advisable to use silicon-containing metal melts of the following comopositions, %:

| Composition I | | Composition II | |
|---|---|---|---|
| silicon | 8 to 15 | silicon | 4 to 12 |
| coppoer | the balance. | gold | the balance. |
| Composition III | | | |
| silicon | 25 to 40 | | |
| nickel | the balance. | | |

Therefore, the method according to the present invention is based on the capability of certain elements to form volatile halides. The term "volatile halides" as used herein means halogen-containing, e.g. chlorine- and fluorine-containing compounds which under normal conditions (T=25° C. or 298° K. and P=1 atm) exist in the gas phase, as well as halogen-containing compounds such as fluorine- and chlorine-containing compounds where temperature of transition from the liquid to the gas phase at a pressure of 1 atm does not exceed 300° C. (573° K.).

In the following Table are listed the elements whose fluorides and chlorides under normal conditions (T==298° K., P=1 atm) exist in the gas phase, as well as elements whose fluorides and chlorides have a temperature of transition from the liquid to the gas state at a pressure of 1 atm below 300° C. (573° K.).

The treatment of a sample of an inorganic material containing the elements enumerated in the following Table with a reagent comprising a fluorine- or chlorine-containing compound, i.e. a non-volatile halide, or a complex fluoride, results in the formation through the reaction between the halogen and the elements incorporated in the sample composition, of volatile halides which are extracted into the gas phase and then are subjected to the quantitative determination in that phase. The term "non-volatile halides" as used herein means halogen-containing compounds such as fluorine and chlorine-containing ones which have a melting point of at least 800° C. (1073° K.) and whose temperature at the beginning of thermal dissociation exceeds the melting point. These compounds are exemplified by fluorides of rare-earth metals, fluorides of alkali-earth metals, fluorides of transition metals of the group of iron, chlorides of rare-earth metals, chlorides of alkali metals and chlorides of alkaline-earth metals.

TABLE

| Element | Fluoride | Phase at 298° K. | Temperature of liquid-gas transition, °K. | Chloride | Phase at 298° K. | Temperature of liquid-gas transition, °K. |
|---|---|---|---|---|---|---|
| Al | — | — | — | $AlCl_3$ | solid | 453 |
| As | $AsF_3$ | liquid | 336 | $AsCl_3$ | liquid | 395 |
| B | $BF_3$ | gas | — | — | — | — |
| C | $CF_4$ | gas | — | — | — | — |
| Cr | $CrF_5$ | liquid | 390 | $CrCl_4$ | liquid | 435 |
| Ge | $GeF_4$ | gas | — | $GeCl_4$ | liquid | 357 |
| Ga | — | — | — | $GaCl_3$ | solid | 573 |
| Jr | $JrF_6$ | solid | 326 | — | — | — |
| Mo | $MoF_6$ | liquid | 309 | $MoCl_5$ | solid | 532 |
| Nb | $NbF_5$ | solid | 499 | $NbCl_5$ | solid | 519 |
| Os | $OsF_6$ | solid | 477 | — | — | — |
| P | $PF_3$ | gas | — | $PCl_3$ | liquid | 348 |
| Pd | $PdF_4$ | liquid | 320 | — | — | — |
| Re | $ReF_6$ | liquid | 321 | — | — | — |
| Ru | $RuF_5$ | solid | 545 | — | — | — |
| Pb | — | — | — | $PbCl_4$ | liquid | 400 |
| Sb | $SbF_5$ | liquid | 423 | $SbCl_5$ | liquid | 445 |
| Si | $SiF_4$ | gas | — | $SiCl_4$ | liquid | 330 |
| Sn | — | — | — | $SnCl_4$ | liquid | 386 |
| Ta | $TaF_5$ | solid | 502 | $TaCl_5$ | solid | 507 |
| Te | $TeF_6$ | gas | — | $TeCl_5$ | solid | 505 |
| Ti | $TiF_4$ | liquid | 557 | $TiCl_5$ | liquid | 409 |
| U | $UF_6$ | solid | 329 | $UCl_6$ | solid | 550 |
| V | $VF_5$ | solid | 384 | $VCl_4$ | liquid | 437 |
| W | $WF_6$ | gas | — | $WCl_5$ | solid | 549 |
| Hg | — | — | — | $HgCl_2$ | solid | 573 |
| Mn | — | — | — | $MnCl_4$ | liquid | 384 |

DETAILED DESCRIPTION OF THE INVENTION

In the determination of such elements as Al, As, B, C, Cr, Ge, Ga, Ir, Mo, Nb, Os, P, Pd, Re, Ru, Pb, Sb, Si, Sn, Ta, Te, Ti, U, V; W, Hg, Mn the treatment of a sample of an inorganic material with a halogen-containing reagent may be carried out according to the present invention in a number of its embodiments.

The most versatile embodiment contemplates the dissolution of a sample of an inorganic material in a bath of a metal melt with a melt layer of a reagent—a non-volatile metal halide formed on its surface. In this case the quantitative chemical analysis of the sample of the inorganic material is effected in a vacuum-melting unit using a mass-spectrometer as a gas analyzer connected to the extraction part of the unit. A a crucible placed into an extraction furnace is charged with a bath material, for example nickel, copper, gold or platinum, and a non-volatile halide such as nickel fluoride, cobalt fluoride, copper fluoride, lanthanum fluoride, lanthanum chloride, and sodium chloride. The extraction furnace is evacuated to a residual pressure of $(1-5) \times 10^{-6}$ mm Hg, the crucible with the charge is heated to melt the bath material and the non-volatile halide. Upon melting no intermixing of the metal and halide melts occurs and the molten halide is in the crucible as a liquid slag on the surface of the molten metal bath. On completion of melting, the analyzed sample of the inorganic material is charged into the crucible. After dissolution of the sample in the bath of the molten metal at the melt-slag interface, an interaction between the halogen with the elements incorporated in the sample composition occurs along with the formation of volatile halides which are extracted to the gas phase. The quantitative determination of the elements incorporated into the sample composition is carried out using a mass-spectrometer by measuring intensity of characteristic lines of the volatile halide in the mass spectrum of the gas-phase. Instead of mass-spectrometry for the quantitative determination of elements in the gas phase, other methods of gas analysis, e.g. IR-spectroscopy, manometric or volumetric methods may be used.

The extraction in the above-described embodiment of the method according to the present invention may be carried out not only under vacuum but in the atmosphere of an inert gas such as helium as well. In this case for the quantitative determination of elements in the gas phase the method of gas chromatography or the method of chromatomass-spectrometry can be used.

It should be noted that the above-mentioned dissolution of a sample of an inorganic material in a bath of a metal melt with the formation, on the bath surface, of a layer of a non-volatile metal halide may be effected in any desired sequence, though the above-described one is preferred.

Usually, the melting of the metal bath and the non-volatile halide is effected in a graphite or corundum crucible. However, graphite and corundum may contain contaminating amounts of boron, phosphorus and certain metal impurities. Upon the interacting with the liquid halide slag, these impurities form volatile halides creating undesirable background during the analysis, thus lowering the analysis sensitivity and reproducibility of its results. For this reason, in the analysis of inorganic materials for the content of boron, phosphorus and metal elements, it is preferable to use a crucible made of a fluorine-containing material such as fluorphlogopite having the composition $KMg_3AlSi_3O_{10}F_2$ and the melting point of 1,270° C., as well as fluorapatite, lepidolite, parisite, roulandite, and humite. It is preferable that the preliminary treatment of the crucible of a fluorine-containing material be effected at a temperature 100°–150° C. lower than the melting point of the crucible material at a under vacuum of $10^{-3}$ to $10^{-4}$ mm Hg which makes it possible to remove all impurities from the crucible in the form of volatile fluorides formed upon the interaction of the impurities with fluorine contained in the crucible material.

When a crucible is made of a fluorine-containing material, the formation of a melt layer of a reagent—nonvolatile metal fluoride on the surface of a metal melt bath may be effected as a result of interaction of the metal melt with the crucible material.

Another embodiment of the treatment of a sample of an inorganic material containing at least one of the elements Al, As, B, C, Cr, etc., comprises dissolution of the sample in a melt of a reagent—complex fluorides of alkali metals such as in a melt of fluoroniobates, fluorotitanates, fluorotantalates of alkali metals or in mixtures of these salts, as well as in melts of mixtures of complex fluorides with chlorides of alkali metals. The use of this mode of the sample treatment is preferable in the analysis of inorganic materials—metals of Groups IV and V (titanium, zirconium, hafnium, tantalum, niobium, vanadium), rare-earth metals and oxides of these metals that are very soluble in melts of complex fluorides. The composition of mixtures of complex fluorides or complex fluorides with chlorides of alkali metals is selected so as to ensure a relatively low (450° to 800° C.) melting point of the mixtures, low vapor tension of the melt and high halogenating ability. The quantitative analysis of the chemical composition of the sample is carried out in a vacuum-melting unit using a mass-spectrometer as a gas analyzer which is connected to the extraction part of the unit. A sample and a weighed portion of a complex salt or a mixture of salts is placed into a crucible. The crucible is placed into an extraction furnace, evacuated to a residual pressure of $(1-5)\times10^{-6}$ mm Hg and the crucible with the change is heated until the fluorine-containing salt (or mixture of salts) is molten. The analyzed sample of the inorganic material is dissolved in the fluorine-containing salt melt. The interaction of fluorine with the elements incorporated in the sample of the inorganic material results in the formation of volatile fluorides which are extracted into the gas phase and quantitatively determined in the gas phase by means of a mass spectrometer through measurements of the intensity of characteristic lines of the volatile halide in the mass-spectrum of the gas phase.

In the described embodiment the operation of melting complex fluorides or mixtures thereof with chlorides and the operation of the sample dissolution in the melt may be effected either simultaneously as shown above, or successively. The operation of extraction may be carried out in vacuum or in the atmosphere of an inert gas.

In the quantitative analysis of the chemical composition of a sample of inorganic material readily liable to halogenation such as aluminum, titanium, metals of Groups V and VI of the periodic system (niobium, tantalum, vanadium, chromium, molybdenum, tungsten), oxides of these metals, it is preferable to carry out the treatment of the sample by blending a preliminarily disintegrated sample with a powder of a halogen-containing reagent—non-volatile metal halide, followed by heat-treatment of the resulting mixture at a temperature below the melting point of all the components of the mixture. The non-volatile halide is preferably anhydrous fluorides of metals of the group of iron (nickel, cobalt, iron) or chlorides of alkali metals. The heat-treatment of the mixture of the finely divided sample and the powder of the non-volatile halide is conducted under a vacuum of $(1-5)\times10^{-6}$ mm Hg at a temperature of from 500° to 800° C. At these temperatures all components of the mixture are in a solid phase, though diffusive mobility of the atoms is sufficiently high and the process of halogenation proceeds rather intensively. The disintegration of the sample and blending thereof with the powder-like halogenating reagent provides a well-developed contact surface, thus ensuring completeness of the halogenation reaction and extraction of the gase phase of the elements being determined. To carry out the quantitative analysis of the chemical composition, the finely divided sample of the inorganic material in a mixture with the powder of the halogenating reagent such as nickel fluoride is charged into a crucible. The crucible is placed into a resistance furnace connected with a mass-spectrometer, evacuated to a residual pressure of $(1-5)\times10^{-6}$ mm Hg and is heated to the temperature of the beginning of the reaction between the halogen and the element being determined. The initiation of the reaction is judged by the emergence, in the mass-spectrum of the gas phase, of the characteristic lines of the volatile halide formed in the reaction. The mixture is maintained at this temperature until completion of the volatile halide extraction. The completion of the extraction is defined by discontinuation of the growth of intensity of the characteristic lines of the volatile halide in the mass-spectrum of the gas phase. The quantitative determination of the element is effected by measuring the intensity of the characteristic lines of the volatile halide in the mass-spectrum of the gas phase.

In the quantitative chemical analysis composition of an inorganic material containing fluorine and/or chlorine the reagent for the treatment of the samples can be, according to the present invention, a silicon-containing metal melt (bath) and the sample treatment is conducted by dissolving of the sample in this melt. The analysis is effected in a vacuum-melting unit with its extraction part connected to a mass-spectrometer. A bath material, e.g. an alloy nickel-silicon, copper-silicon or gold-silicon, is charged into a crucible. The content of silicon in the alloy should be sufficient to ensure complete extraction of fluorine and/or chlorine from the analyzed sample of the inorganic material a tetrafluoride and/or tetrachloride of silicon. However, the presence of excessive amounts of silicon in the alloy results in the formation of high-melting silicides which hinders the extraction of the volatile silicon halide from the melt. An optimal content of silicon in the alloy nickel-silicon is 25 to 40%, in the alloy copper-silicon—8-15%, and in the alloy gold-silicon—4 to 12%. The minimal melting point of said alloys corresponds to the above-specified silicon content. The crucible with the charge is placed into an extraction furnace, evacuated to a residual pressure of $(1-5)\times 10^{-6}$ mm Hg and heated to the melting temperature of the bath. The analyzed sample of an inorganic material is charged into the resulting melt. After dissolution of the sample in the melt as a result of interaction of silicon with fluorine and/or chlorine contained in the sample there occurs the formation of volatile tetrafluoride and/or tetrachloride of silicon which are extracted to the gas phase and quantitatively determined by measuring intensity of the characteristic lines of tetrafluoride and/or tetrachloride of silicon in the mass-spectrum of the gas phase. In addition to the mass-spectrometry, for the quantitative determination of elements in the gas phase use may be made of, for example, IR-spectroscopy, manometric or volumetric methods.

In the above-described embodiment the extraction may be conducted under vacuum or in an inert gas atmosphere, e.g. in helium. In the latter case, for the quantitative determination of elements in the gas phase, of gas-chromatography or chromato-mass-spectrometry methods can be used.

For a better understanding of the present invention some specific Examples illustrating its embodiments are given hereinbelow. In all of the Examples the weight of the analyzed sample is 0.1 g.

EXAMPLE 1

A low-alloyed carbon steel is analyzed for its silicon and phosphorus content. The analysis is carried out in a vacuum-melting unit with its extraction part connected to a mass-spectrometer. Into a graphite crucible there is charged a bath material—5 g of nickel and a reagent—0.5 g of nickel fluoride. The crucible with the charge is placed into an extraction furnace, evacuated to a residual pressure of $1\times 10^{-6}$ mm Hg and heated to the melting temperature of the bath. Simultaneously with the bath melting there occurs melting of the reagent, i.e. nickel fluoride which forms a layer of liquid slag—molten nickel fluoride—on the surface of the bath of the metal melt. A sample of the material being analyzed is charged into the bath at the bath temperature of 1,450° C. 5 seconds after dissolving the sample in the melt, the extraction to the gas phase of the elements being determined in the form of their volatile fluorides begins. This is evidenced by the emergence of characteristic lines of silicon and phosphorus fluorides in the mass-spectrum of the gas phase. The intensity of the lines is increased and then stabilized thus indicating the completion of the extraction to the gas phase of the elements being determined. The extraction duration is 5 to 7 minutes. The quantitative determination of silicon is effected through the intensity of the characteristic line of 85 a.m.u.; determination of phosphorus—through the intensity of the characteristic line of 69 a.m.u. The results of the measurements give the content of silicon of 0.02%, the content of phosphorus is 0.005%. The accuracy of the determination (relative standard deviation) of silicon is 7%, that of phosphorus is 12%. The sensitivity of the determination of silicon and phosphorus calculated by the $2\sigma$ criterion is equal to $5\times 10^{-6}\%$. The correctness of the determination of silicon and phosphorus is supported by the results of the spectrophotometric analysis.

EXAMPLE 2

The analysis of a low-alloyed carbon steel is carried out to find out the content of silicon, boron and phosphorus. The analysis is conducted on the same unit and under the same conditions as in Example 1, except that use is made of 5 g of platinum as the bath material. The quantitative determination of silicon is effected through the measurement of the intensity of the characteristic line of 85 a.m.u., the quantitative determination of boron—through the measurement of the intensity of the characteristic line of 48 a.m.u., the quantitative determination of phosphorus—by measuring the intensity of the characteristic line of 69 a.m.u. The results of the measurements point to a silicon content of 0.3%, a boron content of 0.04%, a phosphorus content of 0.0009%. The relative standard deviation in the determination of silicon is 4%, in the determination of boron it is 12%, and the standard relative deviation in the determination of phosphorus is 18%. The sensitivity of the determination calculated by the $2\sigma$-criterion is equal to $5.10^{-6}\%$.

EXAMPLE 3

Lanthanum oxide is subjected to analysis for the content of arsenic. The analysis is carried out in a vacuum-melting unit with its extraction part connected to a mass-spectrometer through a molecular separator. Into a graphite crucible a bath material—5 g of platinum is charged. Then the crucible with the charge is placed into an extraction furnace, evacuated to a residual pressure of $5\times 10^{-6}$ mm Hg, heated to the bath melting temperature, whereafter evacuation is stopped and the volume of the extraction furnace is filled with an inert gas i.e. helium, to a pressure of 0.4 mm Hg. The sample to be analyzed is charged into the metal melt bath, followed by the addition of the reagent—0.5 g of lanthanum fluoride which forms, on the surface of the metal melt bath, a layer of a liquid slag, i.e. lanthanum fluoride melt. After the dissolution of the analyzed sample in the metal melt bath with the layer of said liquid slag on its surface, the extraction to the gas phase of the element being determined in the form of a volatile fluoride begins. The extraction in the atmosphere of an inert gas prevents the formation of sorptionally-active lanthanum sublimates and losses of the evolving volatile halide—arsenic fluoride as a result of its sorption on lanthanum sublimates.

The evolved arsenic fluoride is fed, in a mixture with helium, through a molecular separator to a mass-spectrometer. In the molecular separator there occurs the separation of helium from arsenic fluoride which is fed into the mass-spectrometer, wherein its mass-spectrum is recorded. The quantitative determination of arsenic is effected by measuring the intensity of the characteristic line of 113 a.m.u. The results of the measurements show the arsenic content in lanthanum oxide to be 0.0004%. The accuracy of the determination (relative standard deviation) is 23%. The sensitivity of the determination of arsenic calculated by the $2\sigma$—criterion is $5.10^{-6}\%$.

EXAMPLE 4

Iron is subjected to analysis for the content of boron. The analysis is carried out in a vacuum-melting unit connected to a mass-spectrometer. Into a crucible made of fluorphlogopite of the composition $KMg_3AlSi_3O_{10}F_2$ the bath material (5 g of copper) is charged. The crucible with the charge is placed into an extraction furnace, evacuated to a residual pressure of $10^{-4}$ mm Hg and a heat-treatment of the crucible with the bath is effected at a temperature of 1,200° C. (i.e. by about 100° C. below the melting point of fluorphlogopite) for 30 minutes. During the heat-treatment the removal of the impurities from the crucible due to the formation of volatile fluorides and extraction thereof into the gas phase occurs. The metal bath is molten and during the heat-treatment it is saturated with fluorine due to the interaction of the metal melt with the crucible material. The interaction product, i.e. the nonvolatile copper fluoride, forms a layer of liquid slag on the surface of the metal melt. On completion of the heat-treatment the extraction furnace is evacuated to a residual pressure of $10^{-6}$ mm Hg, the crucible temperature is lowered to 1,150° C. and the sample being analyzed is immersed into the melt. After the dissolution of the analyzed sample in the melt the extraction of the element being determined starts in the form of a volatile fluoride passing to the gas phase. 10 minutes after the beginning of the extraction a mass-spectrum of the gas phase is recorded. The quantitative determination of boron is effected by measuring the intensity of the characteristic line of 48 a.m.u. The results of the measurements point to a boron content of 0.0017%. The relative standard deviation is 10%, the determination sensitivity as calculated by the $2\tau$-criterion is $10^{-6}\%$.

EXAMPLE 5

Titanium is subjected to analysis for the content of phosphorus. The analysis is carried out under the same conditions as in Example 4, except that a crucible made of parisite is used. The quantitative determination of phosphorus in the gas phase is conducted through measurements of the intensity of the characteristic line of 69 a.m.u. in the mass-spectrum of the gas phase. The test results indicate the content of phosphorus to be 0.001%. The relative standard deviation is 21%, the sensitivity as calculated for the $2\sigma$-criterion is $2.10^{-5}\%$.

EXAMPLE 6

Metallic praseodymium is subjected to analysis for the content of tantalum. The analysis is carried out in a vacuum-melting unit connected by lines heated to 300° C. to a mass-spectrometer. Into a corundum crucible there is charged a bath material—5 g of a copper-nickel alloy with a copper content of 50% and a reagent—0.5 g of lanthanum chloride. The crucible with the charge is placed into an extraction furnace, evacuated to a residual pressure of $10^{-6}$ mm Hg and heating is effected until melting of the bath. Simultaneously with the melting of the bath, the reagent, lanthanum chloride, also melts and forms, on the surface of the metal melt bath, a layer of liquid slag comprising a melt of lanthanum chloride. At the the metal melt bath temperature of 1,350° C. an analyzed sample is charged thereinto. After the dissolution of the analyzed sample in the melt, the extraction of the element being determined to the gas phase in the form of a volatile chloride begins. 15 minutes after the beginning of the extraction the mass-spectrum of the gas phase is recorded. The quantitative determination of tantalum is effected through measurements of the intensity of the characteristic line of 321 a.m.u. The results of the measurements show the content of tantalum is 0.13%. The relative standard deviation is 6%, the determination sensitivity calculated by the $2\sigma$-criterion is equal to $10^{-5}\%$. The correctness of the determination of tantalum has been proven by the results of an extraction-colorimetric analysis.

EXAMPLE 7

Titanium is subjected to analysis for the content of phosphorus. The analysis is carried out in a vacuum-melting unit connected to a mass-spectrometer. Into a graphite crucible there is charged a reagent—3 g of a complex fluoride comprising potassium fluorotitanate. The crucible with the charge is placed into an extraction furnace, evacuated to a residual pressure of $10^{-6}$ mm Hg and heated to 750° C. Into the resulting melt of the complex fluoride an analyzed sample is immersed. After dissolution of the sample in the melt of the reagent the extraction of the element being determined into the gas phase in the form of a volatile fluoride begins. 20 minutes after the dissolution of the sample in the melt the mass-spectrum of the gas phase is recorded. The quantitative determination of phosphorus is effected by measuring the intensity of the characteristic line of 69 a.m.u. The results of the measurements show the content of phosphorus is 0.0012%, the relative standard deviation is 14%, and the sensitivity calculated for the $2\sigma$-criterion is $5.10^{-6}\%$.

EXAMPLE 8

A vanadium-niobium alloy is analyzed for the content of palladium. The analysis is carried out in a vacuum-melting unit connected to a mass-spectrometer through a molecular separator. Into a graphite crucible there are charged 3 g of a mixture of complex fluorides of alkali metals—potassium fluoroniobate and sodium fluorotantalate in a weight ratio of 2:1. The crucible with the charge is placed into an extraction furnace, evacuated to a residual pressure of $10^{-6}$ mm Hg and heated to the melting temperature of the mixture of complex fluorides. Then evacuation is stopped and the extraction furnace is filled with an inert gas, e.g. helium, to a pressure of 0.4 mm Hg. Into the melt of the mixture of complex fluorides an analyzed sample is immersed.

Palladium fluoride being extracted from the melt to the gas phase is fed, in a mixture with helium, to the mass-spectrometer via the molecular separator; In the molecular separator helium is separated and palladium fluoride is passed to the mass-spectrometer, wherein the mass-spectrum is recorded. The quantitative determination of palladium is effected by measuring the intensity of the characteristic line of 164 a.m.u. The test results give the content of palladium to be 1.42%, the relative standard deviation is 0.8%. The determination sensitivity as calculated by the $2\sigma$-criterion is equal to $10^{-5}\%$. The correctness of the determination of palladium is also proven by the results of X-ray spectral analysis.

EXAMPLE 9

A sample of a mineral raw material (a mixture of oxides of silicon, aluminium and rare metals) is subjected to analysis for the content of uranium. The analysis is carried out in a vacuum-melting unit combined with a chromato-mass-spectrometric system employed as a gas analyzer. Into a graphite crucible there is charged the analyzed sample and 10 g of a mixture consisting of 12% of the reagent—potassium fluoroniobate and 88% of the additive—lithium chloride. The crucible with the charge is placed into an extraction furnace, evacuated to a residual pressure of $10^{-6}$ mm Hg, whereafter the evacuation is discontinued and the furnace space is filled with an inert gas, i.e. helium. The crucible with the charge is heated to a temperature of 780° C.;. The mixture of complex fluoride and chloride is molten and the analyzed sample is dissolved in the melt. The volatile fluorides extracted from the melt to the gas phase are fed, in a mixture with helium, to the mass-spectrometer through the chromatograph. In the chromatograph the gas phase is separated in fractions. By means of the mass-spectrometer, mass-spectra of the chromatographic fractions are recorded simultaneously with the recording of the chromatogram. After the registration of the last peak, identification of the chromatographic peak of uranium hexafluoride is effected using the mass-spectra. The quantitative determination of uranium is effected by measuring the area of the chromatographic peak of uranium hexafluoride. The results of the measurements give the content of uranium to be 0.002%, the relative standard deviation is 18%, the determination sensitivity calculated by the $2\sigma$-criterion is equal to $10^{-5}\%$.

EXAMPLE 10

Vanadium is subjected to analysis for the content of tungsten. The analysis is carried out in a vacuum-melting unit connected to a mass-spectrometer. The sample to be analyzed is charged into a graphite curcible along with 10 g of a mixture consisting of 50% of a reagent—sodium fluoroniobate and 50% of sodium and potassium chlorides (in a weight ratio of 1:1). The crucible with the charge is placed into an extraction furnace, evacuated to a residual pressure of $10^{-6}$ mm Hg and heated to a temperature of 600° C. The mixture of the complex fluoride with potassium and sodium chlorides is molten and the analyzed sample is dissolved in the melt. The volatile tungsten fluoride is extracted from the melt to the gas phase. The mass-spectrum of the gas phase is then recorded. The quantitative determination of tungsten is effected by measuring the intensity of the characteristic line of 279 a.m.u. The results of the measurements give the content of tungsten to be 0.3%, the relative standard deviation is 6%. The determination sensitivity as calculated by the $2\sigma$-criterion is $5 \times 10^{-6}\%$.

EXAMPLE 11

Tantalum is analyzed for the content of tungsten. The analysis is carried out under the same conditions and in the same unit as in the foregoing Example 10. The sample to be analyzed is charged into a graphic crucible with 10 g of a mixture consisting of 96% of the reagent-potassium fluorotantalate and 4% of potassium chloride. The quantitative determination of tungsten by measuring the intensity of the line of 279 a.m.u. in the mass-spectrum of the gas phase gives a tungsten content of 1.2%; the relative standard deviation is 0.5%. The determination sensitivity as calculated for the $2\sigma$-criterion is equal to $5 \times 10^{-6}\%$.

EXAMPLE 12

Niobium pentoxide powder is analyzed for the content of tungsten and molybdenum. Into a corundum crucible there is charged a sample of the powder being analyzed in a mixture with the reagent—3 g of sodium chloride powder. The crucible with the charge is placed into an electric-resistance furnace, evacuated to a residual pressure of $5 \times 10^{-6}$ mm Hg and slowly heated, while checking the variation of the gas phase composition by means of a mass-spectrometer. The appearance of characteristic lines of tungsten chloride (324 a.m.u.) and molybdenum chloride (136 a.m.u.) in the mass-spectrum of the gas phase demonstrates the beginning of the extraction of molybdenum and tungsten from the sample in the form of volatile chlorides. The temperature of the beginning of the extraction is equal to 650°–700° C. The crucible with the charge is added at this temperature until completion of the extraction evidenced by the discontinuation of the growth of intensity of characteristic lines of tungsten and molybdenum chlorides. On completion of the extraction the quantitative determination of tungsten and molybdenum is effected by measuring the intensity of the lines of 324 a.m.u. (tungsten) and 136 a.m.u. (molybdenum) in the mass-spectrum of the gas phase. The results of the measurements gives the content of tungsten to be 0.04% and the content of molybdenum to be 0.003%. The relative standard deviation in the determination of tungsten is 9%, and in the determination of molybdenum it is 16%. The sensitivity of the determination calculated through the $2\sigma$-criterion both for tungsten and molybdenum is equal to $7 \times 10^{-6}\%$. The correctness of the determination of tungsten and molybdenum is also proven by the results of spectrophotometric analysis.

EXAMPLE 13

Gallium arsenide is subjected to analysis for the content of tellurium. Into a graphite crucible there is charged a disintegrated sample in a mixture with a reagent—8 g of nickel fluoride powder. The crucible with the charge is placed into an electric-resistance furnace connected, via an intermediate vessel, to a chromato-mass-spectrometric system. The furnace chamber with the crucible is evacuated to a residual pressure of $3 \times 10^{-6}$ mm Hg, slowly heated to a temperature of 500° C. and maintained at this temperature for 15 minutes. The volatile fluorides extracted from the sample are pumped into the intermediate vessel, wherefrom they are fed to the chromatograph in a current of a carrier gas-helium. The gas phase fractions separated in the chromatograph are successively passed to the mass-spectrometer which is adjusted for recording to a mass-chromatogram at the characteristic line of tellurium hexafluoride of 222 a.m.u. The quantitative determination of tellurium is effected by measuring the area of the mass-chromatographic peak. The results of the measurements give the content of tellurium to be 0.00004%; the relative standard deviation is 27%. The determination sensitivity as calculated by the $2\sigma$-criterion is equal to $10^{-6}\%$.

EXAMPLE 14

A silicon-germanium alloy is subjected to analysis for the content of germanium. The analysis is carried out under the same conditions as in the foregoing Example 13, except that use is made of cobalt fluoride as the fluorination agent. Recording of the mass-chromatogram is effected at the characteristic line of 131 a.m.u. The quantitative determination of germanium is effected by measuring the area of the mass-chromatographic peak. The results of the measurements give the content of germanium to be 4.9%; the relative standard deviation is 0.21%. The determination sensitivity based on the $2\sigma$-criterion is equal to $10^{-6}\%$.

EXAMPLE 15

An aluminum magnesium alloy is subjected to analysis for the content of silicon. A preliminarily disintegrated sample mixed with nickel fluoride powder is charged into a nickel crucible. The crucible with the charge is placed into an electric-resistance furnace connected to a mass-spectrometer, evacuated to a residual pressure of $1 \times 10^{-6}$ mm Hg and slowly heated to a temperature of 550° C. controlling the variation of the gas-phase composition by means of the mass-spectrometer. Completion of the extraction of silicon in the form of a volatile silicon fluoride is defined by the discontinuation of the growth of the intensity of the characteristic line of 85 a.m.u. in the mass-spectrum of the gas phase. The quantitative determination of silicon is effected on completion of the extraction by measuring the intensity of the line of 85 a.m.u. The results of the measurements give the content to be silicon of 0.34%, the relative standard deviation is 0.41%. The determination sensitivity as calculated by the $2\sigma$-criterion is equal to $5 \times 10^{-6}\%$.

EXAMPLE 16

Tantalum is subjected to analysis for the content of fluorine. The analysis is conducted in a vacuum-melting unit connected with a mass-spectrometer. Into a quartz crucible there is charged a reagent—6.5 g of an alloy consisting of 90% copper and 10% silicon. The crucible with the charge is placed into an extraction furnace, evacuated to the residual pressure of $10^{-6}$ mm Hg and heated to the melting temperature of the reagent. Then the melt temperature is increased to 1,200° C. and the analyzed sample is immersed thereinto. 10 minutes after the dissolution of the sample in the melt the extraction of fluorine from the melt to the gas phase in the form of silicon tetrafluoride is completed. The mass-spectrum of the gas phase is then recorded. The quantitative determination of fluorine is effected by measuring the intensity of the characteristic line of 85 a.m.u. in the mass-spectrum. The results of the tests give the content of fluorine to be 0.26%, the relative standard deviation is 2%. The sensitivity as calculated by the $2\sigma$-criterion is equal to $5 \times 10^{-6}\%$. The correctness of the determination of fluorine is evidenced by the results of spectrophotometric analysis with pyrometallurgic opening-up of the sample.

EXAMPLE 17

Zirconium is subjected to analysis for the content of fluorine. The analysis is carried out using the same unit and under the same conditions as in Example 16 hereinabove, but as the reagent use is made of 6.5 g of an alloy consisting of 92% copper and 8% silicon. The quantitative determination of fluorine in the gas phase gives the content of fluorine to be 0.07%, the relative standard deviation is 8%. The sensitivity as calculated by the 2-criterion is equal to $5 \times 10^{-6}\%$.

EXAMPLE 18

Niobium is analyzed for the content of fluorine. The analysis is carried out under the same conditions and using the same unit as in Example 16, except that as the reagent use is made of 10 g of an alloy consisting of 75% nickel and 25% silicon. The results of the measurements give the content of fluorine of 0.002%, the relative standard deviation is 14%. The sensitivity as calculated by the $2\sigma$-criterion is equal to $5 \times 10^{-6}\%$.

EXAMPLE 19

Yttrium oxide is subjected to analysis for the content of fluorine. The analysis is conducted using the same unit and under the same conditions as in Example 16, but using as the reagent 10 g of an alloy consisting of 60% nickel and 40% silicon. The results of the measurements give the content of fluorine to be 0.04%, the relative standard deviation is 10%. The sensitivity as calculated for the $2\sigma$-criterion is equal to $5 \times 10^{-6}\%$.

EXAMPLE 20

Titanium is subjected to analysis for the content of chlorine. The analysis is carried out in a vacuum-melting unit connected with a mass-spectrometer through a molecular separator. All pipelines are heated to a temperature of 200° C. Into a quartz crucible there is charged a reagent—5 g of an alloy consisting of 94% gold and 6% of silicon. The crucible with the charge is placed into the extraction furnace evacuated to a residual pressure of $10^{-6}$ mm Hg and heated to the melting temperature of the reagent. Afterwards, the evacuation is stopped and the furnace working space is filled with an inert gas, i.e. helium, to a pressure of 0.4 mm Hg. At the melt temperature of 1,000° C., the analyzed sample is immersed into the melt. 15 minutes after the dissolution of the sample the extraction of chlorine from the solution to the gas phase in the form of silicon tetrachloride is completed. The extracted silicon tetrachloride is fed, in a mixture with helium, to the mass-spectrometer through a molecular separator. In the molecular separator helium is separated and silicon tetrachloride is fed to the mass-spectrometer, wherein its mass-spectrum is recorded. The quantitative determination of chlorine is effected by measuring the intensity of the characteristic line of 133 a.m.u. The results of the measurements give the content of chlorine to be 0.06%, the relative standard deviation is 6%. The determination sensitivity as calculated for the $2\sigma$-criterion is equal to $5 \times 10^{-5}\%$.

EXAMPLE 21

Zirconium is subjected to analysis for the content of chlorine. The analysis is conducted in the same unit and under the same conditions as in the foregoing Example 20, except that as the reagent use is made of 6.5 g of an alloy consisting of 85% copper and 15% silicon. The analyzed sample is immersed into the melt at a temperature equal to 1,200° C. The quantitative determination to be chlorine is effected by measuring the intensity of the characteristic line of 133 a.m.u. The results of the thus-performed measurements give the chlorine content of 0.03%, the relative standard deviation is 11%. The determination sensitivity as calculated for the $2\sigma$-criterion is equal to $5 \times 10^{-5}$%.

EXAMPLE 22

A metallurgical slag (a mixture of oxides, fluorides and chlorides of alkali and alkali-earth metals) is subjected to analysis for the content of fluorine and chlorine. The analysis is carried out on the same unit and under the same conditions as in Example 20 hereinbefore, but using as the reagent 10 g of an alloy consisting 88% of gold and 12% of silicon. The quantitative determination fluorine is effected by measuring the intensity of the characteristic line of 85 a.m.u. and the quantitative determination of chlorine is effected by measuring the intensity of the characteristic line of 133 a.m.u. The results of the measurements give the content to be fluorine of 2.4%, the content of chlorine is 0.83%. The relative standard deviation in the determination of fluorine is 0.4%, that in the determination of chlorine is equal to 0.9%. The determination sensitivity as calculated for the $2\sigma$-criterion is equal, in the determination of fluorine, to $5 \times 10^{-6}$%; in the determination of chlorine it is equal to $5 \times 10^{-5}$%.

What is claimed is:

1. A method for the quantitative chemical analysis of an inorganic material selected from the group consisting of metals, alloys, metalloids, and compounds thereof, which comprises:
    (a) charging a sample of said inorganic material into a molten bath of a metal and a non-volatile halide, wherein the non-volatile metal halide forms a liquid layer on the surface of the metal, and whose temperature at the beginning of thermal dissociation exceeds the melting point, said inorganic material and said non-volatile halide being of different composition;
    (b) melting said inorganic material in the molten bath, thereby forming one or more volatile halides from the inorganic material;
    (c) extracting said volatile halides into a gaseous phase and quantitatively determining the elemental chemical composition of said volatile halides.

2. The method of claim 1, wherein the formation of the volatile halides from the inorganic material occurs at the interface of the metal and non-volatile halide.

3. The method of claim 2, wherein the quantitative determination of the elements of the volatile halides in the gas phase is accomplished by means such as, mass spectrometry, IR-spectroscopy, or manometric or volumetric methods.

4. The method of claim 1, wherein the extraction in step (c) is carried out in a vacuum or in the atmosphere of an inert gas, or helium.

5. The method of claim 1, wherein the inorganic material contains at least one element selected from the group consisting of Al, As, B, C, Cr, Ga, Ge, Ir, Mo, Nb, Os, P, Pd, Re, Ru, Pb, Sb, Si, Sn, Ta, Te, Ti, U, V, W, Hg, Mn.

6. The method of claim 5, wherein the non-volatile halide is a compound selected from the group consisting of nickel fluoride, cobalt fluoride, copper fluoride, lanthanum fluoride, lanthanum chloride or sodium chloride.

7. The method of claim 5, wherein the metal of the molten bath is selected from the group consisting of nickel, copper, gold or platinum.

8. The method of any of claims 5, 6 or 7, wherein the bath of the metal melt is produced by melting the metal in a crucible of a fluorine-containing material, which has been preliminarily heat-treated at a temperature 100°–150° C. lower than the melting point of the crucible material under vacuum of from $10^{-3}$ to $10^{-4}$ mm Hg.

9. A method according to claim 8, wherein the crucible is made of fluorophlogopite of the composition $KMg_3AlSi_3O_{10}F_2$.

10. The method of claim 5, wherein the non-volatile halides are complex fluorides of alkali metals.

11. The method of claim 10, wherein the complex fluorides of alkali metals are selected from the group consisting of fluoroniobate, fluorotitanate or fluorotantalate of an alkali metal or mixtures thereof.

12. The method of any of claims 10 or 11, wherein the melt of complex fluorides of alkali metals also contain a chloride of at least one alkali metal in an amount of from 4 to 90% of the total weight of the melt.

13. The method of claim 5, wherein the sample of the inorganic material is preliminarily finely divided and mixed with a powder of the non-volatile metal halide, followed by a heat treatment of the resulting mixture at a temperature within the range of from 500° to 800° C. under vacuum of $(1-5) \cdot 10^{-6}$ mm Hg.

14. The method of claim 13, wherein the non-volatile metal halide is a compound selected from the group consisting of nickel fluoride, cobalt fluoride or sodium chloride.

15. The method of claim 1, wherein the inorganic material contains at least one of the elements F or Cl, and the treatment of said sample is effected by dissolving it in a silicon-containing metal melt.

16. The method of claim 15, wherein the silicon containing metal melt has the following composition, %:
    silicon—8 to 15
    copper—the balance.

17. The method of claim 15, wherein the silicon-containing metal melt has the following composition, %:
    silicon—4 to 12
    gold—the balance.

18. The method of claim 15, wherein the silicon-containing metal melt has the following composition, %:
    silicon—25 to 40
    nickel—the balance.

* * * * *